United States Patent [19]
Bireley

[11] Patent Number: 4,936,333
[45] Date of Patent: Jun. 26, 1990

[54] SENSOR SYSTEM
[75] Inventor: Richard L. Bireley, San Diego, Calif.
[73] Assignee: Aquametrics, Inc., San Diego, Calif.
[21] Appl. No.: 306,160
[22] Filed: Feb. 6, 1989
[51] Int. Cl.$^5$ .............................................. A01G 25/16
[52] U.S. Cl. .................................... 137/78.3; 239/64; 239/70; 137/624.12
[58] Field of Search .................... 239/64, 70; 137/78.3, 137/624.11, 624.12

[56] References Cited
U.S. PATENT DOCUMENTS

| | | | |
|---|---|---|---|
| 3,991,375 | 11/1976 | Riggs et al. | 239/64 |
| 4,256,133 | 3/1981 | Coward et al. | 137/78.3 |
| 4,333,490 | 6/1982 | Enter, Sr. | 239/64 |
| 4,541,563 | 9/1985 | Uetsuhara | 137/624.2 |
| 4,545,396 | 10/1985 | Miller et al. | 137/78.3 |
| 4,657,039 | 4/1987 | Bireley et al. | 137/78.3 |
| 4,718,446 | 1/1988 | Simpson | 137/78.3 |

Primary Examiner—A. Michael Chambers
Attorney, Agent, or Firm—Ellsworth R. Roston; Charles H. Schwartz

[57] ABSTRACT

A includes a first capacitance plate, a dielectric covers a first capacitance plate, second capacitance plates are formed by moisture in an area. The capacitance value, dependent upon the second plate formation, controls the frequency of signals produced by an oscillator. This frequency controls the opening and closing of a first switch. A second switch is in a circuit with the first switch and a solenoid. The closing of the second switch is dependent upon the operation of circuitry energized by an alternating voltage. The alternating voltage is modified to extend the zero voltage level period which occurs at the zero cross-over in the negative direction. When this condition occurs, a pulse is generated by the detection circuitry and this pulse causes the second switch to remain closed. When the first switch operates to indicate no need to water the area, the solenoid is energized and an associated relay is opened. This causes a valve providing, in the open state for the watering of the area, to remain closed. The solenoid becomes de-energized to close the relay when either the second switch becomes opened to indicate a failure to produce pulses at the zero crossover or the first switch becomes opened to indicate a need for watering the area. When a button is manually operated, it prevents the pulses from being produced at the zero crossover time of the alternating voltage. This causes the second switch to open, the solenoid to become de-energized and the relay to close. The valve then becomes opened to obtain a watering of the area.

29 Claims, 3 Drawing Sheets

SENSOR SYSTEM

This invention relates to systems for watering an area. More particularly, the invention relates to a system for providing for a watering of the area on an automatic basis or on a manually operated basis and for providing such an operation with a minimal number of power lines. The invention further relates to a system for self-checking the operation of strategic components in the system while the system is operating in the automatic mode.

In recent years, the number of people in the world has increased rapidly. This has been true even though several countries have adopted birth control policies. As the number of people in the world has increased, the need for water for each individual has increased. This has resulted in part from progressive needs in industry. It has also resulted in part from the increasing sophistications in society. Examples of these sophistications are clothes washers and dish washers.

Because of the increasing demands for the use of water, rivers, lakes and streams have often not been found to be sufficient in different areas of the world. Subterraneum supplies of water are now being tapped in progressively increasing amounts. Furthermore, supplies of water are now becoming polluted because people and governments do not dispose of their waste properly. The progressively increasing demands for water and the progressively decreasing supplies of water indicate that water supplies may soon become inadequate in major areas in the world.

Although water supplies appear to be dwindling and demand seems to be increasing, people still wish to live with the charms of nature around them. For example, people wish to retain beautiful gardens in their yards. They also wish to play golf on beautiful courses, partly because they feel that they are communing with nature. Amenities such as these are important in providing people with the opportunity to relax and to overcome the psychological strains imposed upon them in their everday life.

In recent years, an appreciation has grown that the supply of water is decreasing, especially in comparison to the increasing need for water. Because of this, a considerable effort has been made, and significant amounts of money have been expended, to conserve the supply of water and to inhibit the pollution of such supplies. In spite of such efforts and such money expenditure, the progress in conserving water and in preventing pollution has been at best slow and insufficient.

This invention provides a system for watering an area on an automatic basis only when the area requires watering. The system also provides for a manual operation of the system to override the automatic features and to obtain watering even when the area may not require watering. For example, a manual operation may be desired when the automatic system is malfunctioning. The system provides for an automatic response of the system in the automatic mode to insure that strategic components in the system are operating satisfactorily. When the system is found not to be operating satisfactorily, the system automatically reverts to a time clock mode of operation. In the time clock mode, watering occurs after a particular time set by the time clock. The system provides for an operation of the system in the automatic and manual modes using only those power lines normally required for valve operation in a time clock configuration.

In one embodiment of the invention, a sensor indicating the amount of moisture in an area includes a first capacitance plate, a dielectric covering such plate and second capacitance plates formed by the moisture in the area. The capacitance value, dependent upon the second plate formation, controls the frequency of signals produced by an oscillator. This frequency controls the opening and closing of a first switch (e.g. transistor). A second switch (e.g. transistor) is in a circuit with the first switch and a solenoid. The closing of the second switch is dependent upon the operation of circuitry energized by a signal superimposed upon the alternating voltage.

The alternating voltage is modified to produce a timed zero voltage level at a particular time in each voltage cycle (e.g. the zero crossover in the negative direction). When this zero voltage interval occurs, a pulse is generated by a circuit which causes the second switch to remain closed. When the first switch operates to indicate no need to water the area, an associated relay is opened. This causes a valve providing, in the open state, for the watering of the area to remain closed.

The solenoid becomes de-energized to close the relay when either the second switch becomes opened to indicate a failure to produce pulses at the zero crossover or the first switch becomes opened to indicate a need for watering the area. When a button is operated, it prevents the pulses from being produced at the zero crossover of the alternating voltage. This causes the second switch to open and the relay to close. The valve then becomes opened to obtain a watering of the area.

Figure 1:
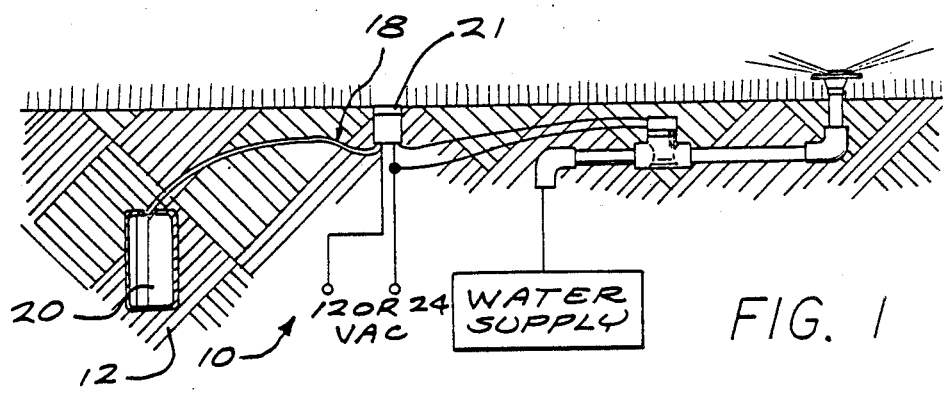
FIG. 1 is a schematic diagram of a system for providing a controlled watering of a patch of earth to maintain a particular amount of moisture as sensed in the patch of earth.

In one embodiment of the invention shown in FIG. 1, a system generally indicated at 10 is provided for controlling the watering of a patch of earth 12. The system 10 includes stages for sensing the amount of water in the patch of earth 12 and for producing signals indicative of such amount of water. The system 10 further includes stages for processing such signals to control the watering of the patch of earth 12 in accordance with the information processed from such signals. Some of the stages are adapted to be disposed at the patch of earth 12 and other stages are adapted to be disposed at a central position displaced from the patches of earth. A coaxial cable generally indicated at 18 provides a communication between a sensor 20 and a valve 21 for controlling the watering around the patch of earth 12.

Figure 2:
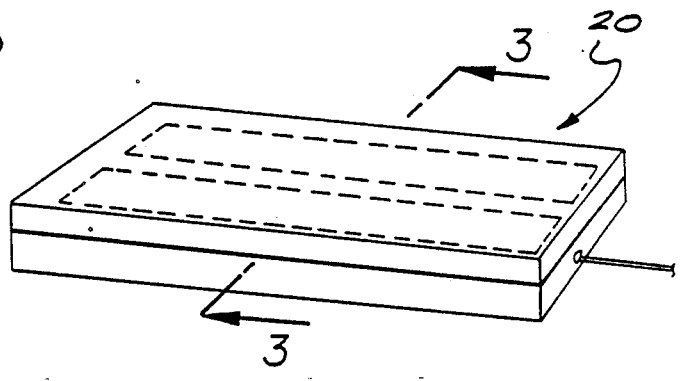
FIG. 2 is a schematic perspective view of a sensor included in an embodiment of the system shown in FIG. 1 for indicating the amount of moisture in the patch of earth.
Figure 3:
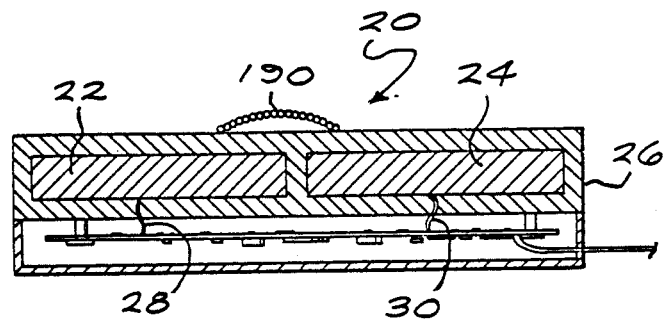
FIG. 3 is a sectional view of the sensors shown in FIG. 2 and is taken substantially on the line 3—3 of FIG. 2.

The sensor 20 is adapted to be disposed in the patch of earth 12 and is shown in further detail in FIGS. 2 and 3. The sensor 20 may be formed in a thin planar relationship. It may include a pair of thin planar electrodes 22 and 24 each of which may be formed from a suitable conductive material such as copper. A layer of a thin dielectric material 26 having electrically insulating properties is disposed in a substantially uniform thickness on the electrodes 22 and 24 to cover the electrodes. The dielectric material 26 has a high dielectric constant. Electrical leads 28 and 30 respectively extend from the electrodes 22 and 24. The electrical leads 28 and 30 are respectively connected to stages designated as a sensing station in FIG. 5. The leads are kept short (less than ½) to minimize interference.

The sensor 20 may be constructed in a manner fully disclosed in co-pending application Ser. No. 004,047 filed by me on Jan. 16, 1987 for "Soil Moisture Monitor". The sensor 20 may be disposed in a system such as that disclosed in co-pending application Ser. No. 004,047.

Figure 4:
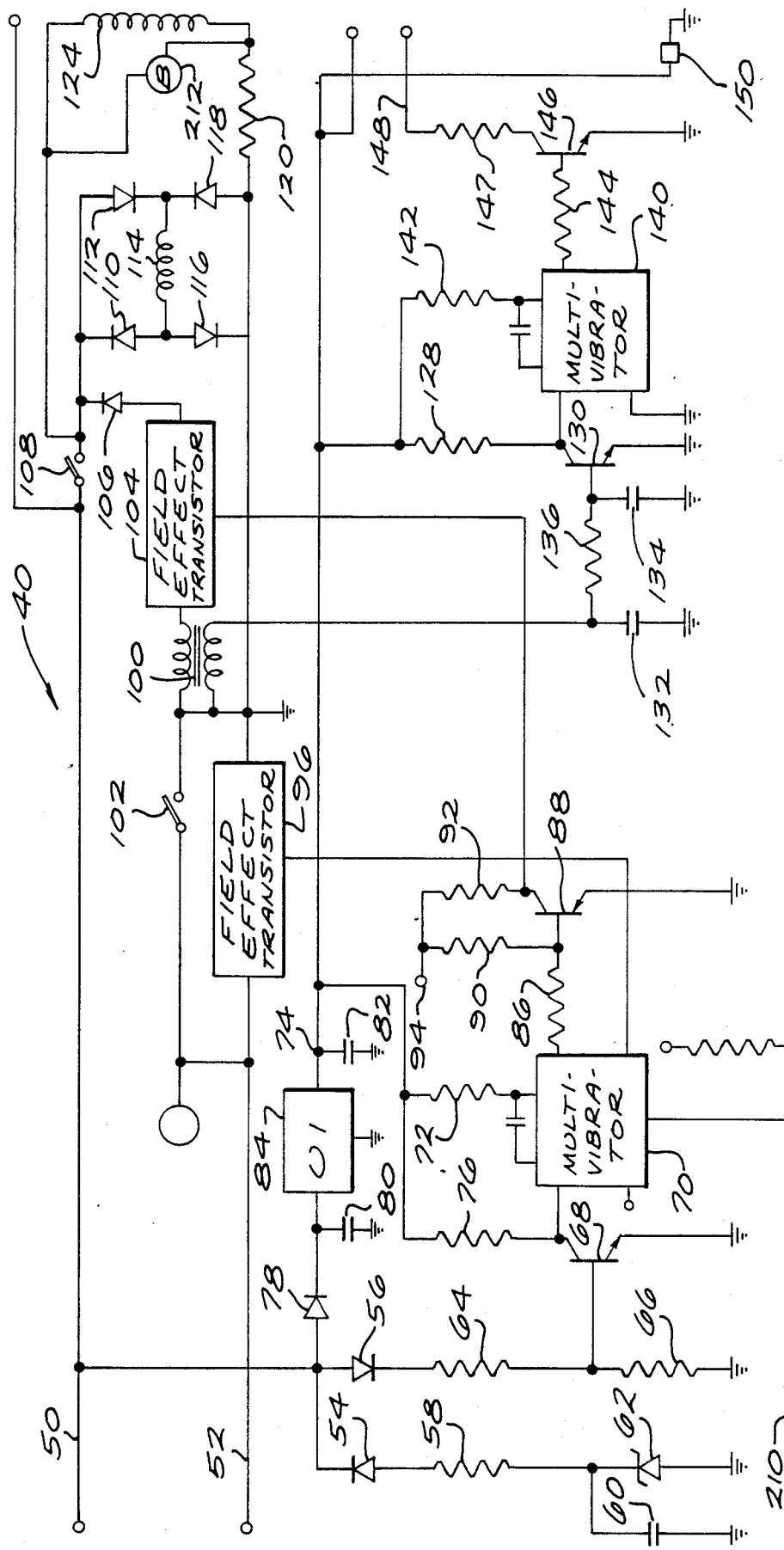
FIG. 4 is a circuit diagram of a portion of an electrical system included at a central station in one embodiment of the invention for modifying the Ac waveform at the zero crossing point.

FIG. 4 illustrates the portion of the system of this invention at the central position. This portion of the system is generally indicated at 40 in FIG. 4. In the circuitry shown in FIG. 4, a suitable alternating voltage such as twenty-four volts (24 V.) is provided between a pair of lines 50 and 52. Connections are made from the line 50 to the cathode of a diode 54 and the anode of a diode 56. The anode of the diode 54 is in series with a resistance 58 and a capacitance 60, one terminal of which is grounded. The resistance 58 and the capacitance 60 may respectively have suitable values such as approximately 1.2K and 10 microfarad. A zener diode 62 is in parallel with the capacitance 60.

A pair of resistances 64 and 66 are in series between the cathode of the diode 56 and ground. The resistances 64 and 66 may respectively have values of 3.3K ohms and 1K ohms. The terminal common to the resistances 64 and 66 is connected to the base of an npn transistor 68, the emitter of which is grounded. The collector of the transistor 68 is connected to an input terminal of a monostable multivibrator 70 which receives a direct voltage through a resistance 72 from a terminal 74. The terminal 74 also introduces a direct voltage through a resistance 76 to the collector of the transistor 68. The resistances 72 and 76 may respectively have values of 33K ohms and 3.3K ohms. The direct voltage is obtained from a rectifier formed by a diode 78, capacitances 80 and 82 and a voltage regulator 84 in a conventional manner.

One output terminal of the monostable multivibrator 70 introduces signals through a resistance 86 to the base of a pnp transistor 88, the emitter of which is grounded. The resistance 86 may have a suitable value such as approximately 8.2K ohms. Resistances 90 and 92 may be respectively connected between a source 94 of a suitable negative voltage such as −16 V. and the base and the collector of the transistor 88. The resistances 90 and 92 may respectively have suitable values such as approximately 20K ohms and 4.7K ohms. The resistances 86 and 90 form a voltage dividing network for introducing a desired voltage to the base of the transistor 88.

The gate of a field effect transistor 96, preferably npn, is common with a second output terminal of the monostable multivibrator 70. The drain of the transistor 96 receives the alternating voltage on the line 52. The source of the transistor 96 is grounded as are first terminals of primary and secondary windings of a transformer 100. A switch 102 is connected between the drain and the source of the transistor 96.

The second terminal of the primary winding in the transformer 100 is connected to the source of a field effect transistor 104, which is preferably pnp. The gate of the transistor 104 receives the voltage on the collector of the transistor 88. A connection is made from the drain of the transistor 104 to the anode of a diode 106, the cathode of which is connected to one terminal of a normally open switch 108. The other terminal of the switch 108 receives the voltage on the line 50.

The cathode of a diode 110 and the anode of a diode 112 are common with the cathode of the diode 106. An inductance 114 bridges the anode of the diode 110 and the cathode of the diode 112 and also bridges the anode of a diode 116 and the cathode of a diode 118. The cathode of the diode 116 and the anode of the diode 118 are grounded as is one terminal of a resistance 120 having a suitable value such as approximately 0.5 ohms. A relay 124 is connected between the second terminal of the resistance 120 and the cathode of the diode 106. The relay 124 may be disposed at the patch of earth 12.

The direct voltage on the terminal 74 is also introduced through a resistance 128 to the collector of an npn transistor 130, the emitter of which is grounded. The resistance 128 may have a suitable value such as approximately 33K ohms. The base of the transistor 130 receives a pulse from the second terminal of the secondary winding in the transistor 100 through a high-pass filter formed by capacitances 132 and 134, each having one terminal grounded, and a resistance 136 connected between the ungrounded terminals of the capacitances. Each of the capacitances 132 and 134 may have a suitable value such as approximately 0.01 microfarad and the resistance 136 may have a suitable value such as approximately 3.9K ohms.

The voltage on the collector of the transistor 130 is introduced to one input terminal of a multivibrator 140, a second input terminal of which is grounded. The multivibrator 140 is biased through a resistance 142 from the terminal 74. An output terminal of the multivibrator 140 passes signals through a resistance 144 to the base of a transistor 146, the emitter of the transistor being grounded. A signal passes through a resistance 146 to one terminal of an indicator such as a lightemitting diode 150, the second terminal of the diode 150 being grounded. The resistances 142, 144 and 146 may respectively have suitable values such approximately 680K ohms, 2.2K ohms and 800 ohms.

Figures 5, 6:
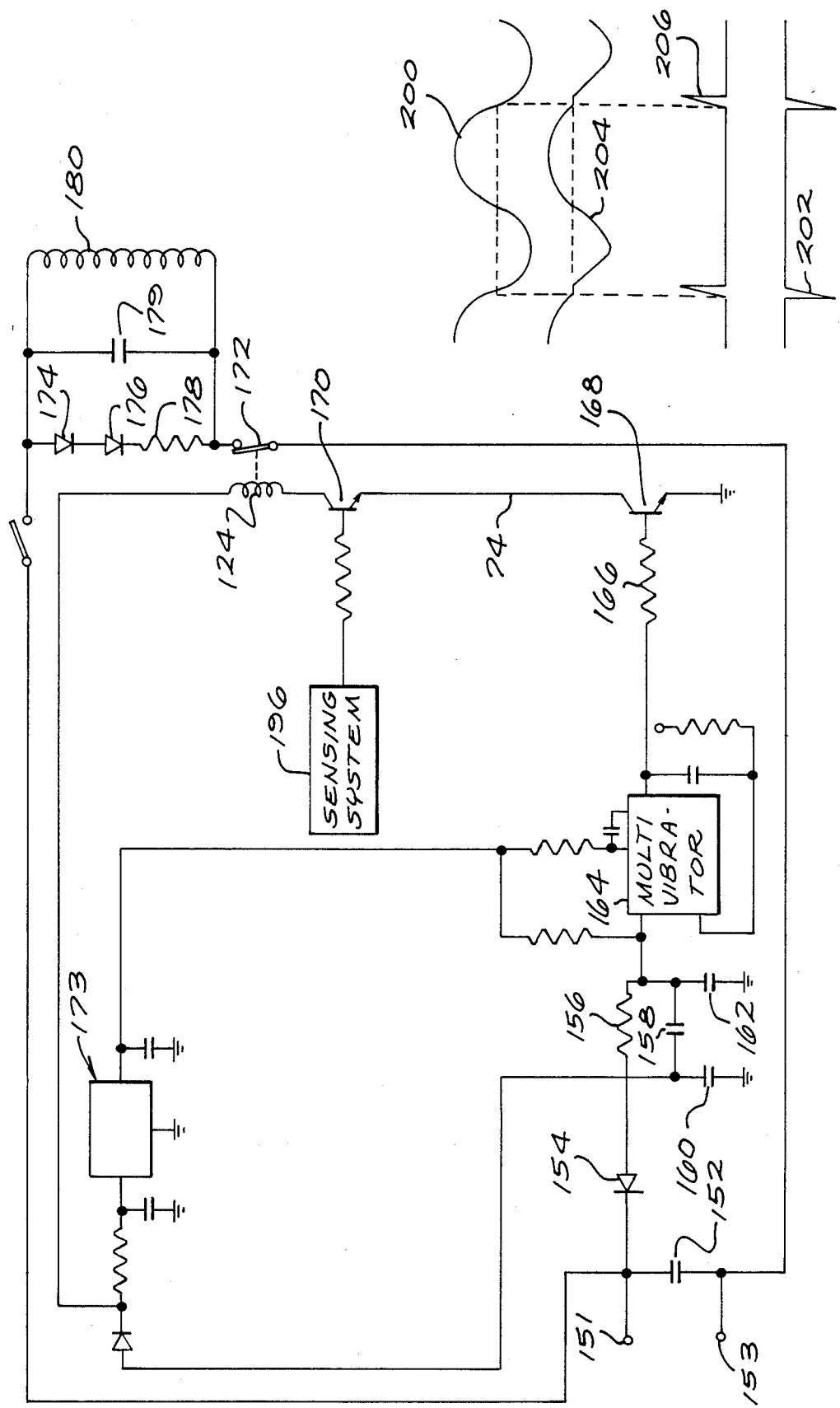
FIG. 5 is a circuit diagram of another portion of the electrical system included in the one embodiment of the invention for providing the controlled watering of the area around the sensor in automatic and manual modes.
FIG. 6 illustrates voltage waveforms at strategic terminals in the circuitry shown in FIGS. 4 and 5.

The system shown in FIG. 5 is disposed at the patch of earth 12. The system shown in FIG. 5 includes a pair of terminals 151 and 153 which respectively receive the voltage at the terminal 50 and on the ungrounded terminal of the secondary winding of the transformer 100 in FIG. 4. The signals on the lines 151 and 153 are introduced to a capacitance 152, which may have a suitable value such as approximately 0.41 microfarad. The voltage on the terminal 151 is introduced to the cathode of a diode 154, the anode of which is connected to first terminals of a resistance 156, a capacitance 158 and a capacitance 160, the second terminal of which is grounded. The second terminals of the resistance 156 and the capacitance 158 are connected to the ungrounded terminal of a capacitance 162. Each of the capacitances 158, 160 and 162 may have suitable value such as 0.1 microfarad and the resistance 156 may have a suitable value such as approximately 33K ohms.

The voltage across the capacitance 162 is introduced to an input terminal of a monostable multivibrator 164 which may be constructed in a conventional manner. The output from the monostable multivibrator 164 is introduced through a resistance 166 to the base of an npn transistor 168. The emitter of the transistor 168 is grounded and the collector of the transistor is connected to the emitter of a transistor 170. The transistor 168 and the transistor 170 are shown in FIG. 5 as being in series with the relay 124 (also shown in FIG. 4). The relay 174 receives the direct voltage from a rectifier 173 connected to the terminal 151. The relay 124 controls the operation of a relay switch 172.

The relay 172 is in series with a diode 174, a light emitting diode 176 and a resistance 178 between the terminals 151 and 153. A capacitance 179 is connected in parallel with the series arrangement of the diodes 174 and 176 and the resistance 178. The resistance 176 may have a suitable value such as approximately 2.2K ohms and the capacitance 179 may have a suitable value such as approximately 0.47 microfarads. A solenoid 180 is in parallel with the capacitance 179. The solenoid 180 controls the opening and closing of the valve (not shown) which provides for the watering of the patch of earth 12 when opened.

The sensor 20 shown in FIGS. 1-3 is disposed in the patch of earth 12 to determine the amount of moisture in the patch of earth. The moisture forms conductive paths 190 (FIG. 3) to the dielectric 26. These conductive paths define capacitances with the electrodes 22 and 24 and the dielectric 26. Each of these conductive paths defines another electrode. As a result, the number of capacitances formed by the multiple conductive paths 190 with the electrode 22 is dependent upon the amount of moisture in the patch of earth 12.

The conductive paths 190 also extend to the dielectric surface covering the electrode 24 to form capacitances with the electrode. The capacitances including the electrode 22 are in series with the capacitances including the electrode 24 because of the electrical leads established by the conductive paths 190. The values of these capacitances are dependent upon the amount of moisture in the patch of earth 12. These capacitances are connected, as a practical matter, through the leads 28 and 30 across the terminals 32 and 34. These capacitances control the frequency of alternating signals produced across the terminals 32 and 34.

The frequency of the alternating signals produced across the terminals 28 and 30 is sensed by a sensing system 196. The sensing system 196 may be constructed in a manner similar to that disclosed in my co-pending application Ser. No. 004,047. The voltage produced by the sensing system is introduced to the base of the transistor 170 to control the state of conductivity in the transistor. When the patch of earth 12 has a relatively high moisture content, the frequency of the signals introduced to the sensing system 196 is relatively high so that a state of conductivity is produced in the transistor 170. The transistor 170 becomes non-conductive when the frequency of the signals introduced to the sensing system 196 becomes relatively low. This indicates that the patch of earth 12 is relatively dry.

An alternating voltage having a suitable amplitude such as approximately twenty-four volts (24 V.) is produced between the terminals 50 and 52 at the central station in FIG. 4. This alternating voltage is illustrated at 200 in FIG. 6. This alternating voltage is rectified by the diode 78, is filtered by the capacitances 80 and 82 and is regulated by the regulator 84. The resultant direct voltage at the terminal 74 is introduced to the collector of the transistor 68 to obtain an energizing of the transistor when the voltage on the base of the transistor exceeds the voltage on the emitter of the transistor. The direct voltage at the terminal 74 is also introduced through the resistance 72 to the monostable multivibrator 70 to provide for an energizing of the multivibrator.

The positive half of the alternating voltage at the terminals 50 and 52 is introduced through the diode 56 to the base of the transistor 68 to make the transistor conductive. A relatively low voltage is accordingly introduced from the collector of the transistor 68 to the multivibrator 70 to obtain the production of a voltage on the lower output terminal of the multivibrator in FIG. 4 for maintaining the field effect transistor 96 conductive.

As the alternating voltage between the terminals 50 and 52 passes through the zero-crossover in the negative-going direction, the transistor 68 becomes non-conductive. This causes the multivibrator 70 to become triggered to produce a negative-going pulse for an instant of time. This negative-going voltage pulse is illustrated at 202 in FIG. 6.

The negative-going voltage pulse 202 is introduced to the gate of the npn field effect transistor 96 to make the transistor non-conductive. A voltage having a waveform such as shown at 204 in FIG. 6 is accordingly produced in the transistor 96. As will be seen, the voltage waveform 204 corresponds to the voltage waveform 200 except for the portion of the waveform where the voltage pulse 202 is produced. In this portion, no voltage is produced in the waveform 204.

During the time that a relatively high voltage is produced on the lower output terminal of the multivibrator 70, a low voltage is produced on the upper output terminal of the multivibrator. This voltage produces a state of conductivity in the transistor 88 and causes a voltage approaching ground to be produced on the collector of the transistor. This voltage causes the field effect transistor 104 to remain non-conductive.

When the multivibrator 70 produces the negative-going voltage pulse 202 on the lower terminal, a positive high voltage pulse 206 is produced on the upper output terminal of the multivibrator. This voltage pulse causes the transistor 88 to become non-conductive and the negative voltage on the terminal 94 to appear on the collector of the transistor. The negative voltage on the collector of the transistor 88 is introduced to the gate of the field effect transistor 104 to produce a state of conductivity in the field effect transistor.

Upon the production of a state of conductivity in the transistor 104, a continuous circuit is produced which includes the primary winding of the transformer 100, the field effect transistor 104, and the diode 106. During the time that the circuit including the relay 124 is operating properly, energy in the solenoid discharges through the primary winding of the transformer 100 when the transistor 104 becomes conductive. As will be seen from the subsequent discussion, when the relay 124 is energized, the valve controlling the watering of the patch of earth 12 is opened to allow watering.

The discharge of energy through the primary winding of the transformer 100 from the relay 124 causes a voltage to be induced in the secondary winding of the transformer. This pulse is filtered by the filter formed by the capacitances 132 and 134 and the resistance 136 so that only the filtered pulse at relatively low frequencies in such induced voltage passes to the base of the transistor 130. This causes high frequency noise to be eliminated. This low frequency pulse may have a waveform corresponding substantially to that of the pulse 206 in FIG. 6.

The pulses 206 are introduced to the transistor 130 to make the transistor conductive. The resultant low voltage pulse on the collector of the transistor 130 triggers the multivibrator 140. The multivibrator 140 has a time constant which is longer than the time between successive ones of the pulses 206. As a result, a substantially constant voltage is introduced from the multivibrator 140 to the base of the transistor 146 to maintain the transistor conductive during the time that the circuitry shown in FIG. 4 is operating properly and the solenoid 124 remains energized. The resultant signal on the line 148 is accordingly introduced to the light emitting diode 150. The light emitting diode 150 accordingly becomes illuminated to indicate that the solenoid 124 is being energized and that the the circuitry shown in FIG. 4 is operating satisfactorily to produce the pulses 202 and 206 in FIG. 6.

FIG. 5 shows the circuitry at the central position for controlling the operation of the relay 124 in accordance with the operation of the circuitry shown in FIG. 4. The circuitry shown in FIG. 5 includes the terminals 151 and 153 which receive the voltage corresponding to the waveform 204 in FIG. 6. Only the negative half of this waveform is able to pass through the diode 154. Only the high frequencies in this waveform are able to pass through the filter formed by the capacitances 160 and 162 and the resistance 156. The signals introduced to the multivibrator 164 accordingly have a waveform corresponding to that illustrated at 206 in FIG. 6.

The signals from the filter trigger the multivibrator 164 to a particular state and maintain the multivibrator in this state as long as the signals continue to be provided in the successive cycles from the filter formed by the capacitances 158, 160 and 162 and the resistance 164. A direct voltage is accordingly introduced from the multivibrator 164 to the base of the transistor 168 to maintain the transistor in a conductive state.

The transistor 170 operates in a conductive state during the time that no water has to be provided to the patch of earth 12. Current accordingly flows through the relay coil 124 during the time that the patch of earth 12 does not have to be watered and the circuitry shown in FIG. 4 continues to operate properly The relay coil 124 is energized as long as the circuitry shown in FIG. 4 continues to produce signals for maintaining the transistor 168 conductive. Furthermore, the relay switch 172 remains open to prevent the solenoid 180 from being energized. Since the solenoid 180 controls the operation of the valve (not shown) for obtaining the watering of the patch of earth 12, the patch of earth 12 is not watered.

When the patch of earth 12 has to be watered because it is dry, the sensor produces a signal which causes the transistor 170 to become non-conductive. The relay 124 accordingly becomes de-energized and the relay switch 172 becomes closed to obtain an energizing of the solenoid 180 and an opening of the valve (not shown) for watering of the patch or earth 12.

Similarly if the waveform 204 is not produced by the circuitry shown in FIG. 4 or if the transistor 168 becomes non-conductive, the relay coil 124 will become de-energized and the relay switch 172 will become closed. Current accordingly flows through a circuit including the terminals 151 and.153, the diode 174, the light emitting diode 176, the resistance 178 and the relay switch 172. The alternating voltage between the terminals 151 and 153 is also introduced to the solenoid 180 and the relay switch 172 to energize the solenoid. The valve (not shown) controlling the watering of the patch of earth 12 accordingly becomes opened to obtain a watering of the patch of earth 12. Watering of the patch of earth 12 under such circumstances is desirable to insure that the patch of earth cannot become excessively dry.

The system described above is intended to operate in an automatic mode to provide a controlled watering of the patch of earth 12 only when the patch of earth requires watering as indicated by the sensor shown in FIG. 2. However, it may sometimes be desired to obtain an operation of the system under certain circumstances in a mode other than an automatic mode. For example, it may be desired to obtain an operation of the system in a manual mode under certain circumstances. One of these circumstances may occur when it is desired to apply fertilizer, requiring an extended watering period.

A switch 210 (FIG. 4) located at the central station may be manually operated to produce an operation of the system in the manual mode. This causes a biasing voltage to be introduced to the monostable multivibrator 70 to prevent the multivibrator from being triggered at the zero cross-overs in successive cycles of the alternating voltage between the terminals 50 and 52. Since the multivibrator 70 cannot be triggered in the successive cycles of the alternating voltage, the pulses 202 cannot be produced. This prevents the multivibrator 164 in FIG. 5 from being triggered in the successive cycles of the alternating voltage to maintain the transistor 168 conductive. Since the transistor 168 is no longer conductive, the solenoid 124 is de-energized, the relay switch 172 is closed and the solenoid 180 is energized. As a result, the valve (not shown) becomes opened to obtain a watering of the patch of earth 12.

The system described above has certain important advantages. For example, it provides for a watering of the patch of earth 12 on an automatic basis under controlled circumstances. Furthermore, the watering of the patch of earth 12 on an automatic operation can be manually overridden at any time by a closure of the switch 210.

The system described above also has other advantages of some importance. For example, it provides for a constant check to insure that the system is operating properly in the automatic mode. This includes a constant check as to the proper operation of the solenoid 124 and also of the components for producing the pulses 202 and 206. The proper operation in the automatic mode of the system shown in FIG. 5 is indicated by a meter 212 at the central station.

There are further important advantages to the system shown in FIGS. 4 and 5. Operation of the system in the automatic and manual modes and the constant check of the proper operation of the system are provided even though the system shown in FIG. 4 is at the central station and the system shown in FIG. 5 is at the patch of earth 12. The fail-safe
operation of the system insures against interruption of the water supplied to the turf or crop and subsequent loss or damage.

Although this invention has been disclosed and illustrate with reference to particular embodiments, the principles involved are susceptible for use in numerous other embodiments which will be apparent to persons skilled in the art. The invention is, therefore, to be limited only as indicated by the scope of the appended claims.

I claim:

1. In combination for controlling the opening and closing of a valve regulating the watering of a particular area in accordance with the amount of moisture in the area,
    a sensor for indicating the amount of moisture in the particular area,
    first means responsive to the indications from the sensor for producing a first signal having first characteristics during times with less than a particular amount of moisture in the particular area and having second characteristics during times with at least the particular amount of moisture in the particular area,
    a relay having first and second states of operation for operating the valve when the relay is in the first state of operation,
    means for providing an alternating signal,
    second means responsive to the alternating signal for normally providing a second signal periodically having first characteristics, and
    means connecting the relay in a circuit with the first means and the second means (a) for obtaining an operation of the relay in the second state during the time that the first signal has the second characteristics and the second signal periodically has the first characteristics and for obtaining an operation of the relay in the first state during the time that the first signal has the first characteristics or the second signal does not periodically have the first characteristics.

2. In a combination as set forth in claim 1,
    means manually operative to discontinue the periodic production of the first characteristics in the second signal.

3. In a combination as set forth in claim 2,
    means responsive to the alternating voltage for providing the alternating voltage with particular characteristics,
    means responsive to the production of the particular characteristics in the alternating voltage and to the production of the first characteristics in the relay for obtaining the periodic production of the second signal with the first characteristics, and
    means responsive to the manual operation of the manually operative means for preventing the periodic production of the second signal with the first characteristics.

4. In combination as set forth in claim 2,
    the sensor including a first capacitance plate and a dielectric and the moisture in the area defining second capacitance plates to form a capacitance with the first capacitance plate and the dielectric, and
    the value of the capacitance controlling the production of the respective one of the first and second characteristics in the first signal.

5. In combination for controlling the opening and closing of a valve regulating the watering of a particular area in accordance with the amount of moisture in the particular area,
    sensor means for providing signals having characteristics indicating whether or not the particular area needs additional watering,
    means for providing an alternating voltage,
    solenoid means normally energized by the alternating voltage,
    means responsive to the alternating voltage for periodically checking the energizing of the solenoid means,
    means connected in a circuit with the checking means for energizing the solenoid means during the time that the sensor means indicates that additional watering is not needed and the checking means periodically indicate that the solenoid means are being energized, and
    relay means for opening the valve when the sensor means indicates that additional watering is needed or when the checking means fails to indicate periodically that the solenoid means are being energized.

6. In a combination as set forth in claim 5,
    manually operative means for providing a watering of the area, and
    means for overriding the periodic checking by the checking means to obtain a de-energizing of the solenoid means when the manually operative means is manually operated.

7. In a combination as set forth in claim 5,
    the checking means including means for altering the characteristics of the alternating voltage in a particular manner in each cycle of the alternating voltage and further including means responsive to the altering in the characteristics of the alternating voltage in each cycle of the alternating voltage and to the indications by the sensor means of no need to water the particular area for energizing the solenoid means.

8. In a combination as set forth in claim 7,
    manually operative means for providing a watering of the particular area, and
    means for overriding the periodic checking by the checking means to obtain a deenergizing of the solenoid means when the manually operative means is manually operated,
    the sensor means including a first capacitance plate and a dielectric covering the first capacitance plate and the water in the area constituting second capacitance plates and forming capacitances with the first capacitance plate and the dielectric to provide indications of the need of additional water in the area in accordance with the value of the capacitances.

9. In combination for controlling the opening and closing of a valve regulating the watering of a particular area in accordance with the amount of moisture in the particular area,
    sensor means for sensing the amount of the moisture in the particular area,
    solenoid means operable in energized and de-energized states,
    relay means operative in open and closed states and associated with the solenoid means for operation in one of the open and closed states in accordance with the energizing and de-energizing of the solenoid means,
    means for normally energizing the solenoid means to obtain an operation of the relay means in the open state, the relay means being constructed to be closed when the solenoid means is de-energized, means for periodically testing the operation of the solenoid means to produce periodically a control signal during the time that the solenoid is being energized, and means for connecting the sensor means and the periodically testing measn in a circuit to maintain the solenoid means energized during the time that the sensor means indicates no need for watering the area and the control signal is being periodically produced.

10. In a combination as set forth in claim 9, means manually operative for preventing the periodic production of the central signal by the periodically testing means.

11. In a combination as set forth in claim 10, means for providing an alternating voltage, means for modifying the alternating voltage to provide a hiatus in the voltage at a particular instant in each cycle of the alternating voltage, the periodically testing means being operative during the hiatus in each cycle of the alternating voltage to produce the control signal periodically during the time that the solenoid means is energized, and the circuit means being operative to energize the solenoid means during the time that the control signal is periodically produced by the periodically testing means and the sensor means indicates no need for watering the area.

12. In a combination as set forth in claim 10, means for providing an alternating voltage periodically having zero crossover positions, means for interrupting the alternating voltage at a particular one of the zero crossover positions in each cycle of the alternating voltage, means responsive to the interruptions in the alternating voltage at the particular one of the zero crossover positions in each cycle of the alternating voltage for receiving energy from the solenoid means to produce energy pulses, and means responsive to the energy pulses for continuing to produce the control signal periodically during the time that the solenoid means is energized.

13. In a combination as set forth in claim 12, means manually operative to discontinue the periodic production of the control signal and to obtain the closing of the relay means.

14. In a combination as set forth in claim 13, the sensor means including a first capacitance plate and a dielectric covering the first capacitance plate and the water in the area forming a second capacitance plate and the capacitance formed by the capacitance plates and the dielectric having a value indicating whether the area needs additional water.

15. In combination for controlling the opening and closing of a valve regulating the watering of a particular area in accordance with the amount of moisture in the particular area, sensor means for sensing the amount of moisture in the particular area, solenoid means having energized and de-energized states, relay means associated with the solenoid means to provide for an opening of the valve during the time that the solenoid means is de-energized and for a closing of the valve during the time that the solenoid means is energized, first means for normally providing for an energizing of the solenoid means, means connected in a circuit with the sensor means and the normally energized solenoid mean for obtaining a periodic checking of the energizing of the solenoid means by the circuit means to maintain the energizing of the solenoid means during the time that the first means provides for an energizing of the solenoid means and the sensor means indicates a sufficient amount of water in the particular area, and means manually operated for de-activating the circuit means to obtain a de-energizing of the solenoid means.

16. In a combination as set forth in claim 15, the first means including:

means for providing an alternating voltage, means for modifying the alternating voltage in each cycle to provide a particular change in the alternating voltage at a particular time in each cycle of the alternating voltage, and means responsive to the particular change in the alternating voltage in each cycle and to the energy from the solenoid means for maintaining the relay means in the closed state unless the sensor means senses an insufficient amount of moisture in the area or there is not the particular change in the alternating voltage in each cycle of the alternating voltage.

17. In a combination as set forth in claim 15, the manually operative means being operative to prevent the alternating voltage from being modified at the particular time in each cycle of the alternating voltage.

18. In a combination as set forth in claim 16, the sensor means including a first capacitance plate and a dielectric covering the first capacitance plate and the water the particular area defining second capacitance plates and the first and second capacitance plates defining capacitances having a value dependent upon the amount of moisture in the area, means including the first and second capacitance plates and the dielectric for producing signals at a frequency dependent upon the values of the capacitance, and the first means being operative to obtain an energizing of the solenoid means dependent upon the frequency of such signals.

19. In combination for controlling the opening and closing of a valve regulating the watering of a particular area in accordance with the amount of moisture in the particular area, a sensor for indicating the amount of moisture in the particular area, first means responsive to the indications from the sensor for producing a first signal having first characteristics for occurrences less than a particular amount of moisture in the particular area and having second characteristics for occurrences at least equal to the particular amount of moisture in the particular area, a solenoid for operating the valve, the solenoid having energized and de-energized states, means for providing an alternating voltage, control means responsive to the alternating voltage and to the energy from the solenoid in the energized state of the solenoid for periodically providing signals indicating the energized state of the solenoid, means for connecting the solenoid, the first means and the control means in a conduit for continuing to energize the solenoid during the time that the control means periodically provides the signal indicating the energized state of the solenoid and the first means produces the first signal with the second characteristics, and a relay for operating the valve, the relay having open and closed states and operable in the closed state to open the valve for the flow of water in the particular area, the relay being associated with the solenoid to become opened during the time that the solenoid is de-energized and to become closed when the solenoid is energized.

20. In a combination as set forth in claim 18, means manually operative to prevent the control means from periodically producing the signal indicating the energized state of the solenoid.

21. In a combination as set forth in claim 19, regulating means for acting upon the alternating voltage to provide for an operation of the control means at a particular time in each cycle of the alternating voltage to periodically provide signals indicating the energized state of the solenoid, the control means being responsive to the operation of the regulating means and to the energized state of the solenoid for periodically producing the signal indicating the energized state of the solenoid, and the manually operative means being operative to de-activate the regulating means.

22. In a combination as set forth in claim 20, the regulating means being operative to produce a second signal upon each zero crossover of the alternating voltage in a particular direction, the manually operative means including means responsive to the signals from the regulating means and to the energized state of the solenoid for introducing a voltage to the control means to continue to energize the solenoid.

23. In a combination as set forth in claim 21, the control means including first and second switching means each having open and closed states, the first switching means being responsive to the signals from the first means to become closed when the signals from the first means have the second characteristics, and the second switching means being responsive to the signals from the controls means to become closed when the control means produce the signals indicating the energized state of the solenoid.

24. In a combination as set forth in claim 22, the sensor means including a first capacitance plate and a dielectric material and the water in the particular area producing second capacitance plates defining capacitances with the first capacitance plates, the first means including oscillator means responsive to the values of the capacitances produced by the first and second capacitances plates for producing signals having a frequency representative of such capacitance values, and the first switching means being operative in the closed state dependent upon the frequency of the signals from the oscillator means.

25. In combination for controlling the opening and closing of a valve regulating the watering of a particular area in accordance with the amount of moisture in the particular area, a sensor for indicating the amount of moisture in the particular area, first means responsive to the indications from the sensor for producing a first signal having first characteristics during times with less than a particular amount of moisture in the particular area and having second characteristics during times with at least the particular amount of moisture in the particular area, relay means having first and second states of operation for operating the valve when the relay means is in the first state of operation and for preventing the operation of the valve when the relay means in the second state, second means for periodically testing the operation of the relay means to provide a second signal periodically having first characteristics when the relay means is operative in the second state, third means responsive to the first means and the second means (a) for obtaining an operation of the relay means in the second state during the time that the first signal has the second characteristics and the second signal periodically has the first characteristics and (b) for obtaining an operation of the relay means in the first state when the first signal has the first characteristics or the second signal periodically does not have the first characteristics.

26. In a combination as set forth in claim 25, means manually operative to discontinue the periodic production of the first characteristics in the second signal.

27. In a combination as set forth in claim 25, the sensor means including a first capacitance plate and a dielectric covering the first capacitance plate and the water in the particular area defining second capacitance plates and the first and second capacitance plates defining capacitances having a valve dependent upon the amount of moisture particular in the area.

28. In a combination as set forth in claim 27, third means including the first and second capacitance plates and the dielectric for producing signals at a frequency dependent upon the values of the capacitances, and the second means being operative to obtain an operation of the relay means in the first and second states dependent upon the frequency of the signals from the third means.

29. In a combination as set forth in claim 28, means manually operative to discontinue the periodic production of the first characteristics in the second signal.

* * * * *